US010429349B2

United States Patent
Joneit

(10) Patent No.: US 10,429,349 B2
(45) Date of Patent: Oct. 1, 2019

(54) METHOD FOR DETERMINING ELECTRICAL CONDUCTIVITIES IN SAMPLES BY MEANS OF AN EDDY CURRENT SENSOR

(71) Applicant: Fraunhofer-Gesellschaft zur Foerderung der angewandten Forschung e.V., Munich (DE)

(72) Inventor: Dieter Joneit, Glashuette (DE)

(73) Assignee: FRAUNHOFER—GESELLSCHAFT ZUR FOERDERUNG DER ANGEWANDTEN FORSCHUNG E.V., Munich (DE)

( * ) Notice: Subject to any disclaimer, the term of this patent is extended or adjusted under 35 U.S.C. 154(b) by 614 days.

(21) Appl. No.: 14/770,887

(22) PCT Filed: Mar. 14, 2014

(86) PCT No.: PCT/EP2014/055101
§ 371 (c)(1),
(2) Date: Aug. 27, 2015

(87) PCT Pub. No.: WO2014/146982
PCT Pub. Date: Sep. 25, 2014

(65) Prior Publication Data
US 2016/0003776 A1 Jan. 7, 2016

(30) Foreign Application Priority Data
Mar. 19, 2013 (DE) .................. 10 2013 004 990

(51) Int. Cl.
*G01N 27/82* (2006.01)
*G01N 27/90* (2006.01)
(52) U.S. Cl.
CPC ..... *G01N 27/9046* (2013.01); *G01N 27/9086* (2013.01)

(58) Field of Classification Search
CPC .................. G01N 27/9046; G01N 27/9086
See application file for complete search history.

(56) References Cited

U.S. PATENT DOCUMENTS

| 5,394,084 A | 2/1995 | Snyder |
| 5,541,510 A | 7/1996 | Danielson |
| 2012/0043962 A1 | 2/2012 | Wang et al. |

FOREIGN PATENT DOCUMENTS

| DE | 19610844 A1 | 10/1996 |
| DE | 19940843 A1 | 3/2001 |

OTHER PUBLICATIONS

Meletic et al. "The ωσ method: A new contactless comparison method for measuring electrical conductivity of nonferromagnetic conductors" Rev. Sci. Instrum., vol. 68, No. 9, Sep. 1997, pp. 3523-3527.*

(Continued)

*Primary Examiner* — Melissa J Koval
*Assistant Examiner* — Courtney G McDonnough
(74) *Attorney, Agent, or Firm* — Jacobson Holman, PLLC.

(57) ABSTRACT

In the method for determining the electrical conductivity in samples by an eddy current sensor, an alternating electrical field is excited at a known measurement frequency, an alternating electromagnetic field which is directed against the alternating electrical field is thereby formed, detected by a suitable detector, and the complex impedance is determined, which procedure is repeated at different known measurement frequencies, once in air and once with the same measurement frequencies at a calibration body, differences of the real and imaginary portions and of the measured values in air and over the calibration body are then divided by the respective measurement frequency, wherein a product $\omega\sigma$ is associated with each value pair $\Delta R/\omega$ and $\Delta X/\omega = \Delta L$ in accordance with the associated measurement frequency w (Continued)

and the known conductivity a of the calibration body and a ωσ locus is presented in a Nyquist diagram.

6 Claims, 3 Drawing Sheets

(56) References Cited

OTHER PUBLICATIONS

García-Martín et al. "Non-Destructive Techniques Based on Eddy Current Testing", Sensors 2011, pp. 2525-2565.*
Loveday et al. "Evaluation of Organic Coating with Electrochemical Impedance Spectroscopy", JCT Coatings Tech. , Aug. 2004, pp. 46-52.*
Blitz et al: "Eddy current testing of metals", Materials and Design, London, GB, Bd. 8, Nr. 6, Nov. 1, 1987 (Nov. 1, 1987), Seiten 340-345, XP024153867, ISSN: 0261-3069, DOI.
Mileti et al.: "The method: A new contactless comparison method for measuring electrical conductivity of nonferromagnetic conductors", RSI, Bd. 68, Nr. 9, Jan. 1, 1997.

* cited by examiner

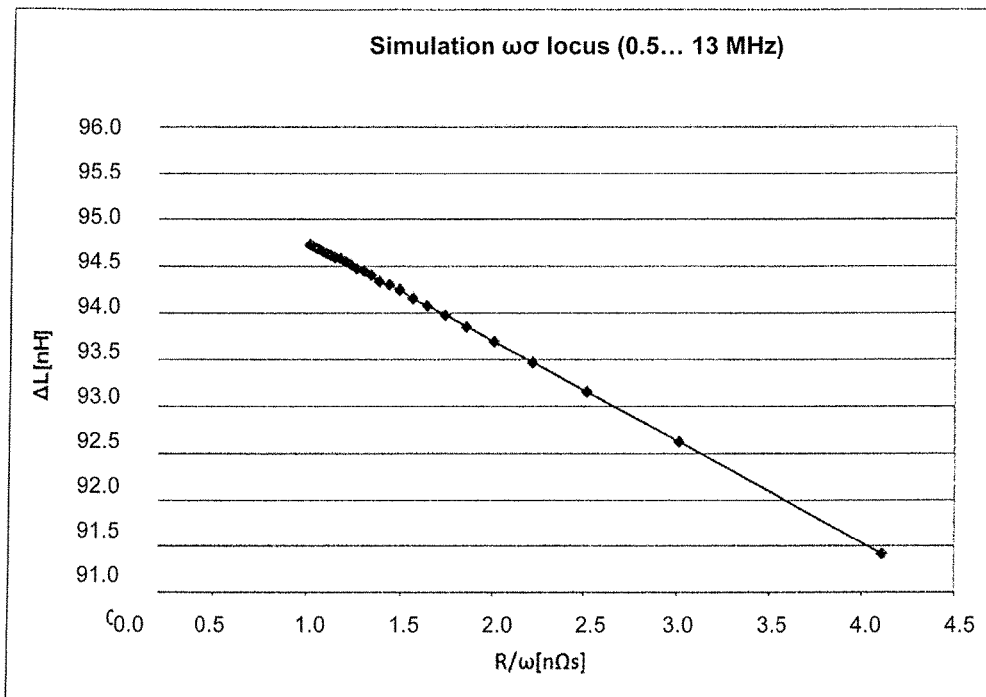
ωσ locus over Cu 100% IACS calculated with a simulation and derived therefrom
Fig. 1
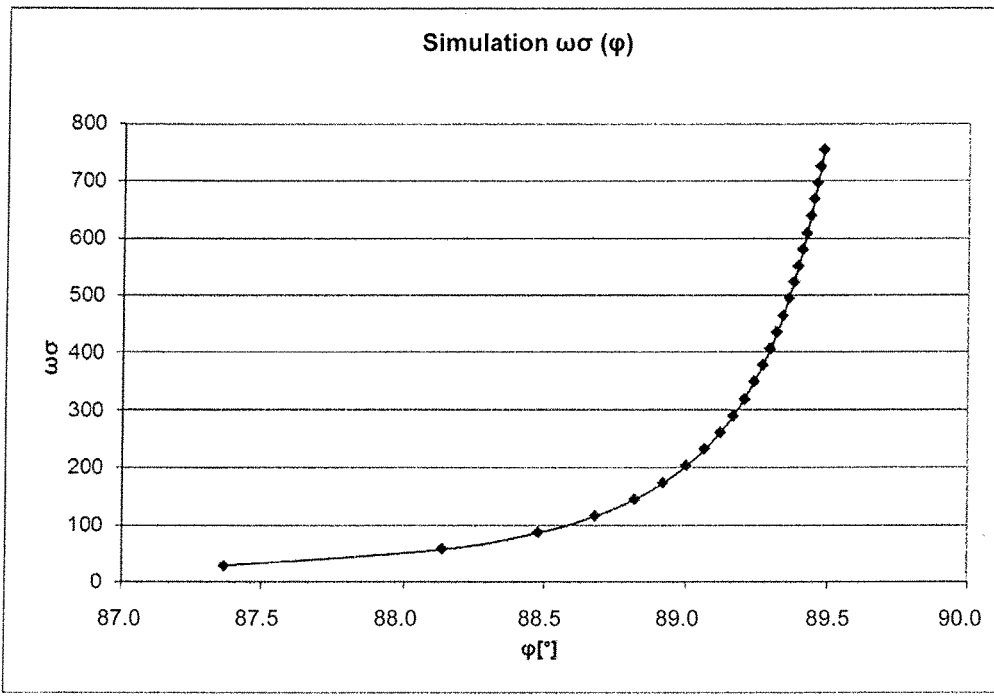
$\omega\sigma = f(\varphi) = \tan(\Delta L/(R/\omega))$     Fig. 2

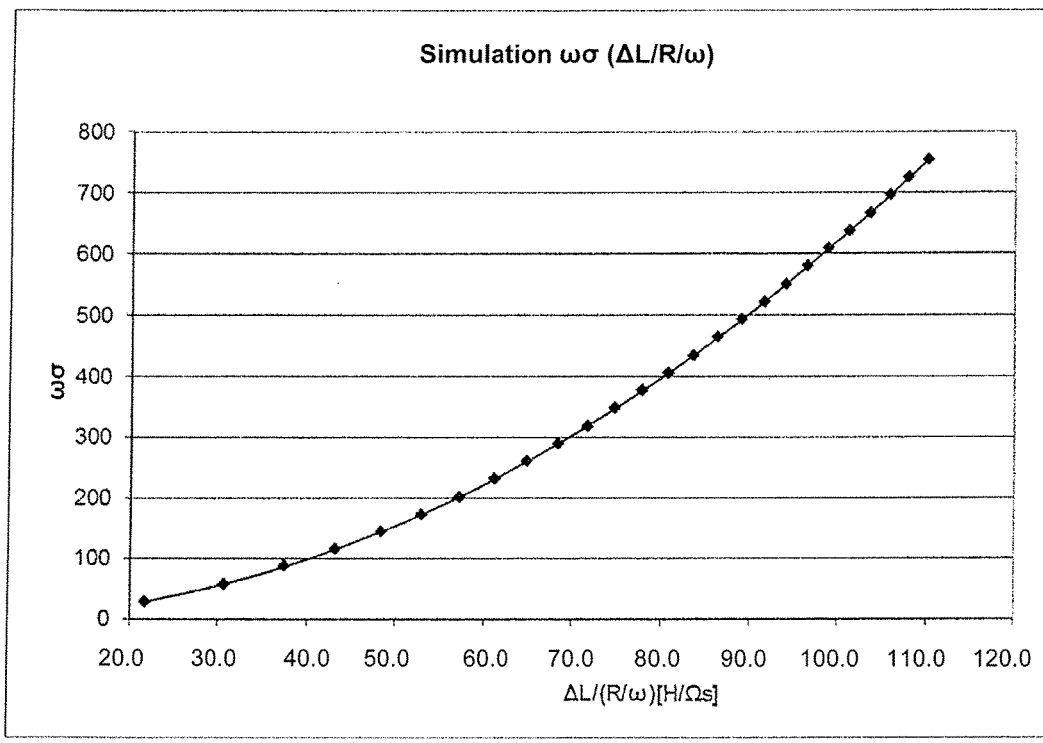
$\omega\sigma = f(\Delta L/(R/\omega))$    Fig. 3
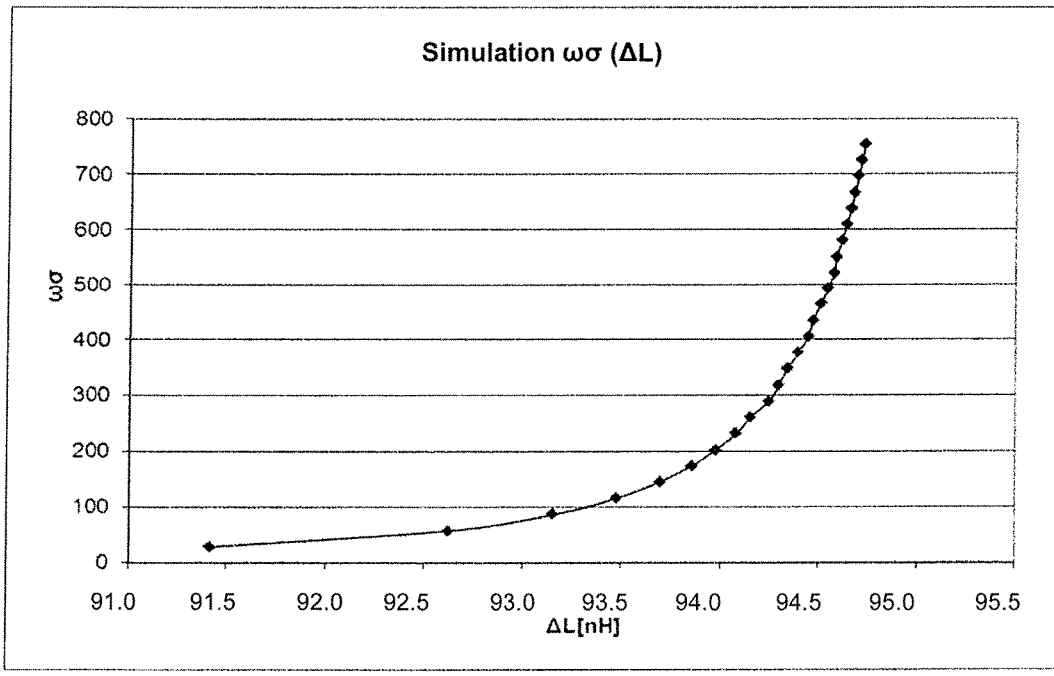
$\omega\sigma = f(\Delta L)$    Fig. 4

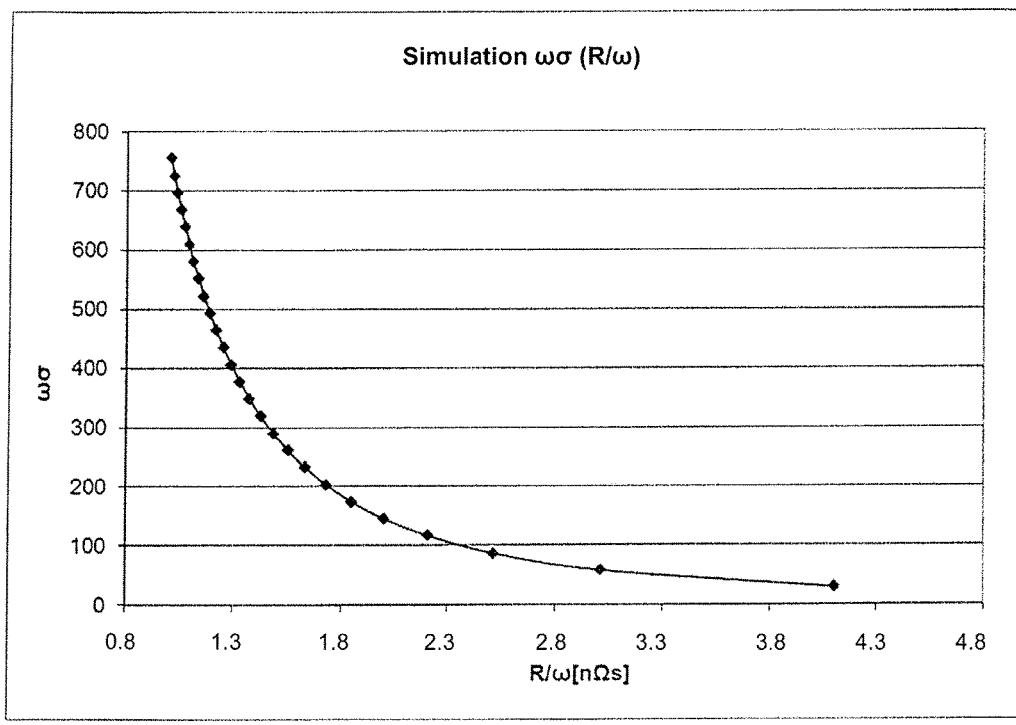
ωσ = f(R/ω)  Fig. 5

METHOD FOR DETERMINING ELECTRICAL CONDUCTIVITIES IN SAMPLES BY MEANS OF AN EDDY CURRENT SENSOR

The invention relates to a method for determining the electrical conductivity in samples by means of an eddy current sensor which can be used, for example, for a non-destructive examination of samples. Eddy current sensors can be used for the detection of flaws (e.g. cracks, pores, inclusions) in samples, but also for the determination of material parameters such as the electrical conductivity σ or, for example, also the magnetic permeability μ or for the determination of thicknesses of metal layers or of other layers.

In this respect, an electrical coil is typically used which generates a corresponding electric field with an electric alternating current. If a sample or a calibration body formed from or by a suitable material enters into the alternating electric field, electric eddy currents are generated in the sample which in turn result in the formation of an alternating electromagnetic field which is directed against the electric field of the electrical coil and whose parameters can be detected using a receiver coil or also using another suitable detector.

In eddy current examinations, the influence of an electrically conductive material of a sample on the magnetic field of an electrical coil is determined by determining the real and imaginary portions R and X of the changed magnetic field.

For this purpose, an electric alternating current having a known circular frequency is typically supplied to an eddy current sensor once via a transmission amplifier. It simultaneously serves as a reference signal with whose aid the real and imaginary portions R and X can be determined in a demodulator from the signal received by the eddy current sensor. The respective real portion and the respective imaginary portion R and X are in this respect only the respective amount of the electric voltage and not the respective impedance Z.

In eddy current examinations, the influence of a material on the magnetic field of an electrical coil is determined by determining the real and the imaginary portion of the electrical coil. These values are very dependent on the frequency and on the spacing of the electrical coil from the material or from a probe to be examined (lift-off). Their association with material properties such as the electrical conductivity σ takes place via calibrations which are only valid in a tightly restricted range of the frequency, of the lift-off and of the material values. At the same time, there is the problem that usually there are not sufficiently exact and gradated material samples available for the determination of the calibration curves.

It has therefore previously been attempted to determine the measured values from the limited number of calibration points by utilizing suitable mathematical functions and by means of interpolation. This is very complex and is associated with an increased error. A constant known spacing between the surface of a sample and the eddy current sensor or at least its detector must be observed during the measurement.

It is therefore the object of the invention to provide options for determining the electrical conductivities in samples which allow a simple performance and determination of the electrical conductivity with increased precision.

This object is achieved in accordance with the invention by the method in accordance with claim 1. Advantageous embodiments and further developments can be realized using features designated in the subordinate claims.

The invention will first be presented very generally and explained in principle and with its backgrounds.

An eddy current sensor is typically operated at a frequency f which in this respect represents the actual measurement frequency f. However, since the circular frequency ω, which results as ω=2π*f, is typically used in the determination of impedance values, the circular frequency ω will generally be called the measurement frequency in the following.

The generated electromagnetic field F(A) of an eddy current sensor can be functionally described by the following equation $$F(A) = \int_V \left( \frac{1}{2} \frac{B^2}{\mu} - SA + \frac{1}{2} j\omega\sigma A^2 \right) dV$$

In this respect, A is the vector potential, S is the current density in the coil, B is the magnetic flux density, μ is the magnetic permeability of the sample material, σ is the electrical conductivity of the material, ω is the circular frequency and V is the volume over which integration is carried out.

The first term in this respect describes the magnetic field, the second term the exciting electric field, that is the electromagnetic field generated by the electric coil current, and the third term the eddy current field in the material of a sample.

On a closer observation of this expression, it can be recognized that the material properties are not contained in all three terms. The first term is only influenced by the permeability μ. With a non-magnetic material, the permeability μ is approximately as large as in air, that is, 1.0. The second term is fully independent of the material, and only in the third term is the electric conductivity σ contained as the product with the circular frequency ω.

It is known that the imaginary portion X divided by the circular frequency ω produces the inductance L.

If the impedance Z of the electric coil for different electric conductivities σ and circular frequencies ω is calculated by means of simulation, it can be recognized that with the same product values ω*σ, the inductance L and the phase angle φ between the real portion R and the imaginary part X adopt identical values. If the real portion R obtained in the simulation is likewise divided by the respective circular frequency ω, this value is also identical. Tables 1 to 3 show this.

Table 1 contains the impedance values calculated using a simulation program for a circular frequency ω of 1 MHz and conductivities σ in the range from 16 to 1.6×10⁹ S/m.

Table 2 indicates the impedance values for the fourfold circular frequency ω, that is, 4 MHz, with a simultaneous quartering of the electrical conductivities σ. The same is indicated in Table 3 for a tenfold circular frequency ω and a tenth of the electrical conductivity σ with respect to Table 1, that is, here in the range between 1.6 to 1.6*10⁸ S/m. This shows that the product ω*σ is always of an equal amount in the same table lines.

(The value ΔL is the difference of the inductance L in air from the inductance over the material, that is $$\Delta L = L_{in\ air} - L_{over\ material.}\ )$$

TABLE 1

1 MHz

| σ | R | X | Z | φ | L | R/ω | ΔL |
|---|---|---|---|---|---|---|---|
| Air |  | 3.0418 | 3.0418 |  | 484.12 |  |  |
| 1.6E+01 | 0.00022 | 3.0418 | 3.0418 | 89.996 | 484.12 | 0.035247 | 0.00 |
| 1.6E+02 | 0.00197 | 3.0417 | 3.0417 | 89.963 | 484.10 | 0.314293 | 0.02 |
| 1.6E+03 | 0.01654 | 3.0379 | 3.0380 | 89.698 | 483.50 | 2.632182 | 0.62 |
| 1.6E+04 | 0.08694 | 2.9873 | 2.9885 | 88.333 | 475.44 | 13.837180 | 8.68 |
| 1.6E+05 | 0.15915 | 2.7664 | 2.7710 | 86.708 | 440.29 | 25.330256 | 43.83 |
| 1.6E+06 | 0.09342 | 2.5581 | 2.6698 | 87.908 | 407.14 | 14.869330 | 76.98 |
| 1.6E+07 | 0.03526 | 2.4777 | 2.4779 | 89.185 | 394.33 | 5.612128 | 89.79 |
| 1.6E+08 | 0.01176 | 2.4517 | 2.4517 | 89.725 | 390.19 | 1.872195 | 93.93 |
| 1.6E+09 | 0.00378 | 2.4434 | 2.4434 | 89.911 | 388.88 | 0.601958 | 95.24 |

TABLE 2

4 MHz

| σ | R | X | Z | φ | L | R/ω | ΔL |
|---|---|---|---|---|---|---|---|
| Air |  | 12.1670 | 12.1670 |  | 484.12 |  |  |
| 4.0E+00 | 0.00089 | 12.1670 | 12.1670 | 89.996 | 484.12 | 0.035238 | 0.00 |
| 4.0E+01 | 0.00790 | 12.1670 | 12.1670 | 89.963 | 484.10 | 0.314293 | 0.02 |
| 4.0E+02 | 0.06615 | 12.1520 | 12.1520 | 89.688 | 483.50 | 2.632142 | 0.62 |
| 4.0E+03 | 0.34776 | 11.9490 | 11.9540 | 88.333 | 475.44 | 13.837339 | 8.68 |
| 4.0E+04 | 0.63659 | 11.0660 | 11.0840 | 86.708 | 440.29 | 25.329858 | 43.83 |
| 4.0E+05 | 0.37369 | 10.2320 | 10.2390 | 87.908 | 407.13 | 14.869091 | 76.99 |
| 4.0E+06 | 0.14104 | 9.9106 | 9.9116 | 89.185 | 394.33 | 5.611969 | 89.79 |
| 4.0E+07 | 0.04705 | 9.8066 | 9.8068 | 69.725 | 390.19 | 1.872115 | 93.93 |
| 4.0E+08 | 0.01513 | 9.7737 | 9.7737 | 89.911 | 388.88 | 0.601942 | 95.24 |

TABLE 3

10 MHz

| σ | R | X | Z | φ | L | R/ω | ΔL |
|---|---|---|---|---|---|---|---|
| Air |  | 30.4180 | 30.4180 |  | 484.12 |  |  |
| 1.6E+00 | 0.00221 | 30.4180 | 30.4180 | 89.936 | 484.12 | 0.035241 | 0.00 |
| 1.6E+01 | 0.01975 | 30.4170 | 30.4170 | 89.963 | 484.10 | 0.314293 | 0.02 |
| 1.6E+02 | 0.16538 | 30.3790 | 30.3800 | 89.688 | 483.50 | 2.632182 | 0.62 |
| 1.6E+03 | 0.86941 | 29.8730 | 29.8860 | 88.333 | 475.44 | 13.837880 | 8.68 |
| 1.6E+04 | 1.59150 | 27.6640 | 27.7100 | 86.708 | 440.29 | 25.330256 | 43.83 |
| 1.6E+05 | 0.93424 | 25.5810 | 25.5980 | 87.908 | 407.14 | 14.869330 | 76.98 |
| 1.6E+06 | 0.35261 | 24.7770 | 24.7790 | 89.185 | 394.33 | 5.612128 | 89.79 |
| 1.6E+07 | 0.11763 | 24.5170 | 24.5170 | 89.725 | 390.19 | 1.872195 | 93.93 |
| 1.6E+08 | 0.03782 | 24.4340 | 24.4340 | 89.911 | 388.88 | 0.601958 | 95.24 |

As can immediately be recognized, the values for the product of the circular frequency and the electrical conductivity $\omega \ast \sigma$ are also of equal amounts in these lines. It results from this that the electrical conductivity $\sigma$ and the circular frequency $\omega$ have an equal influence on the real and imaginary portions R and X, i.e. that the difficult and complex variation of the electrical conductivity $\sigma$ can be replaced with a comparatively simple variation of the circular frequency $\omega$ in a calibration.

When approaching the material of a sample, the inductance L of the electrical coil falls. This can be explained by the fact that the eddy current field generated in the material of the sample is directed against the excited field of the electrical coil. The inductance L is a measure for the energy of the magnetic field and can be calculated from the magnetic flux density B (see functional). It results from this that the difference of the magnetic field strength H without and with the material influence has to be equal to the magnetic field strength H of the eddy current field ($B_{eddy\ current} = B_{in\ air} - B_{over\ material}$).

The increase in the real portion R on approaching the material of a sample is equally a measure for the electric field strength E of the eddy current field.

The division of the real portion R by the circular frequency $\omega$ requires special note. In the simulation, the real portion R of an electrical coil in air is equal to zero since it is considered as an ideal electrical coil in this respect. The value can here immediately be divided by the circular frequency $\omega$. In practice, the real portion R is composed of different proportions, The ohmic resistance of the windings of the electrical coil is a constant and its increase by the skin effect is not linearly dependent on the circular frequency $\omega$. It would be wrong to divide these values by the circular frequency $\omega$. Only the portion which is caused by the effect of the eddy current field generated in the material of a sample results in meaningful values after the division by the circular frequency $\omega$. This proportion can be determined by forming the difference from the real portion R of the electrical coil in air with the same circular frequency $\omega$.

A locus of the product of the circular frequency and of the electrical conductivity is required for the measurement, said locus being determined from the difference of the coil impedance L in air and with respect to the electrical conductivity $\sigma$ defined via a calibration body. This can be seen from the diagram shown in FIG. 1.

The difference of the real portions (divided by the circular frequency $\omega$) is entered on the abscissa and the difference of the inductances $\Delta L$ is entered on the ordinate, A calibration according to the method in accordance with the invention has the following procedure:

Step 1: The impedance Z of the electrical coil in air is measured at different circular frequencies $\omega$.

Step 2: The impedance Z of the electrical coil is measured at the same circular frequencies $\omega$ over a calibration body having a defined electrical conductivity $\sigma$.

Step 3: The differences of real and imaginary portions $\Delta R$ and $\Delta X$ between the values in air and over the material are divided by the respective circular frequency $\omega$ and produce the $\omega\sigma$ locus.

Step 4: The measurement range results from the desired measurement frequency $\omega$ and the range of the electrical conductivity $\sigma$ to be measured. If e.g. electrical conductivities $\sigma$ in the range between 25 S/m and 100 S/m are to be measured at a circular frequency $\omega$ of 1 MHz and if a calibration body having an electrical conductivity$\sigma$ of 50 S/m is available, the circular frequency $\omega$ has to be varied from 500 kHz (for 100 S/m) up to 2 MHz (for 25 S/m). However, an electrical conductivity $\sigma$ of 200 S/m at 250 kHz or 12.5 S/m at 4 MHz can equally be measured with this locus obtained therefrom, The product of the electrical conductivity $\sigma$ and the circular frequency $\omega$ must always be within the calibration limits $\omega^*\sigma$.

The differences of the real and imaginary portions $\Delta R/\omega$ and $\Delta X/\omega=\Delta L$ divided by the circular frequency $\omega$ are again determined in the measurement over an unknown material. A point on the $\omega\sigma$ locus results relative to this. Since the respective measurement frequency $\omega$ is known, the associated electrical conductivity $\sigma$ can now be determined.

If the $\omega\sigma$ loci are calculated by simulation at different spacings of the electrical coil from the surface of a material (sample), the same $\omega\sigma$ points approximately lie on straight lines which correspond to the phase angle $\varphi$ in a first approximation.

A conclusion on a spacing tolerance (lift-off tolerance) of the values can be concluded from this.

This is very logical: If the electrical coil is moved away from the material (surface of a sample), the magnetic field strength H in the material is reduced, which, however, equally produces a reduction of the magnetic field strength H of the eddy current field generated in the material of the sample. The ratio of the exciting field to the eddy current field is expressed by the phase angle $\varphi$ and remains approximately the same. Only the repercussion on the electrical coil is smaller and the precision with which this phase angle $\varphi$ can be determined thus falls.

A function $\omega\sigma=f(\varphi)$ can therefore also be determined from the locus. The phase angle $\varphi$ is determined from the measured difference values $\Delta R/\omega$ and $\Delta X/\omega=\Delta L$; the value $\omega\sigma$ is determined with the phase angle $\varphi$ using this function and from this, by means of the measurement frequency, the conductivity $\sigma$.

Functions $\omega\sigma=f(\Delta R/\omega)$ or $\omega\sigma=f(\Delta L)$ can also be determined from the difference values $\Delta R/\omega$ and $\Delta L$ and the conductivity $\sigma$ can be determined by this.

In the method in accordance with the invention, an alternating electrical field is excited within a sample by means of an eddy current sensor by an alternating electrical voltage applied to a transmitter coil at a known measurement frequency $\omega$ and an alternating electromagnetic field which is directed against the alternating electrical field is thereby formed which is detected by a receiver coil or by a suitable detector and the complex impedance $Z=R+jX$ is determined, with this procedure being carried out at different measurement frequencies $\omega$ once in air and once with the same measurement frequencies at a calibration body with a known electrical conductivity $\sigma$.

The electrical conductivity $\sigma$ of a sample can then be determined in three alternatives named in the following.

In the first alternative, the differences of the real and imaginary portions $\Delta R$ and $\Delta X$ of the measured values in air and over the calibration body are divided by the respective measurement frequency $\omega$. A product $\omega\sigma$ is associated with each value pair $\Delta R/\omega$ and $\Delta X/\omega=\Delta L$ in accordance with the associated measurement frequency $\omega$ and the known conductivity $\sigma$ of the calibration body and a $\omega\sigma$ locus is shown in a Nyquist diagram with these value pairs. With a measured impedance Z and at a measurement frequency $\omega$ at a sample with unknown conductivity $\sigma$, a value pair $\Delta R/\omega$ and $\Delta X/\omega$ of the values in air is associated with those measured values over the sample and a point from the $\omega\sigma$ locus and thus a $\omega\sigma$ value is associated with this value pair $\Delta R/\omega$ and $\Delta X/\omega=\Delta L$. The unknown electrical conductivity $\sigma$ of the sample material is determined from this at the known measurement frequency $\omega$.

In the second alternative in accordance with the invention, on the calibration at a calibration body and a measurement at a sample, the phase angle $\varphi=\tan(\Delta X/\Delta R)$ is calculated and the function of the product $\omega\sigma=f(\varphi)$ is determined instead of the $\omega\sigma$ locus, with a product $\omega\sigma$ being associated with the phase angle $\varphi$ on the measurement of an unknown conductivity $\sigma$ of the sample material using this function and the electrical conductivity $\sigma$ of the sample thus being determined at the known measurement frequency $\omega$.

In the third alternative in accordance with the invention, the quotient $q=\Delta X/\Delta R$ or its reciprocal $1/q$ is calculated in the calibration at a calibration body and a measurement at a sample. Instead of the $\omega\sigma$ locus, the function of the product $\omega\sigma=f(q)$ or $\omega\sigma=f(1/q)$ is determined and a product $\omega\sigma$ is associated with the quotient q or $1/q$ on the measurement of an unknown conductivity $\sigma$ of a sample with this function $f(q)$ or $f(1/q)$ and the electrical conductivity $\sigma$ of the sample material is thus determined.

The respective measurement frequency $\omega$ should be selected in dependence on the respective measurement range of the conductivity $\sigma$ such that the product $\omega\sigma$ lies within the limits of the previously determined $\omega\sigma$ locus. The circular frequency should preferably be selected as the measurement frequency.

In the calibration at a calibration body in air, all the measurement frequencies should be taken into account which are later taken into account in the determination of the electrical conductivity $\sigma$ at samples.

It is also possible to proceed in the invention such that only the difference of the real portion $\Delta R/\omega$ is determined in the calibration at a calibration body and a measurement at a sample. The function of the product $\omega\sigma=f(\Delta R/\omega)$ is determined instead of the $\omega\sigma$ locus; with a product $\omega\sigma$ being associated with the difference $\Delta R/\omega$ on the measurement of an unknown conductivity $\sigma$ of a sample using this function and with thus the electrical conductivity $\sigma$ of the sample being determined.

It is, however, also possible to determine the difference of the imaginary portion $\Delta X/\omega=\Delta L$ in the calibration at a calibration body and a measurement at a sample. The function of the product $\omega\sigma=f(\Delta L)$ is then determined instead of the $\omega\sigma$ locus, with a product $\omega\sigma$ being associated with the difference $\Delta L$ on the measurement of an unknown conductivity $\sigma$ of a sample using this function and the electrical conductivity $\sigma$ of the sample thus being able to be determined.

The selection of the evaluation with the previously named alternatives and options, namely whether the $\omega\sigma$ locus or one of the derived functions are used for the determination of the electrical conductivity $\sigma$, can be carried out in dependence on the respective measurement job. It can be observed in this respect that if the $\omega\sigma$ locus increases or drops very steeply in the desired range, the measurement value fluctuations are larger. If one of the derived functions delivers a more shallowly increasing or dropping curve extent in this range, it should be selected due to the smaller measurement value fluctuations.

In the following Table 4, measurement values and calculated values are indicated with reference to simulation calculations in which an ideal coil for an eddy current sensor and a sample of copper are taken into account. The real portion in air is zero and "L in air" can be calculated from the imaginary portion. The $\Delta L$ is the difference L– "L in air". R– "R in air" is identical to "Real" in the simulation.

The columns Frequency, Real (portion) and (Imaginary portion) are values obtained from the simulation. L and R/$\omega$ are values divided by $\omega$.

The $\omega\sigma$ locus results from the columns in which the values are underlined. R/$\omega$ for the abscissa, $\Delta L$ for the ordinate. A $\omega\sigma$ value is associated for each point of the $\omega\sigma$ locus so that, with a known measurement frequency $\omega$, a value for the corresponding electrical conductivity $\sigma$ can be simply determined.

In columns in which the values are shown in bold as well as the respective column $\Delta L$ or R/$\omega$, the derived functions $\omega\sigma=f(\Phi)$, $\omega\sigma=f(\Delta L/(R/\omega))$, $\omega\sigma=f(/R/\omega)$ and $\omega\sigma=f(\Delta L)$ result together with the $\omega\sigma$ column. "Real" and "Imag" are the values for air; "Cu Real" and "Cu Imag" are the associated values for a sample of copper:

$$\Delta L(\text{"Imag"}-\text{"Cu Imag"})/\omega\sigma$$

$$R/\omega=(\text{"Cu Real"}-\text{"Real"})/\omega\sigma$$

The specific $\omega\sigma$ locus results in an equivalent manner from this from the columns in which the values are underlined.

TABLE 4

P9x5
Copper 58 *10e6 S/M
L in air 484.13 nH

| | Frequency | Real[Ω] | Imag[Ω] | L[nH] | R/ω[nΩs] | ΔL[nH] | ωσ | φ | φ[°] | ΔL/(R/ω) |
|---|---|---|---|---|---|---|---|---|---|---|
| 0 | 0.5 | 0.013215 | 1.2338 | 392.74 | 4.207 | 91.388 | 29 | 1.52480 | 87.36710 | 21.724888 |
| 1 | 1 | 0.019005 | 2.4594 | 391.44 | 3.025 | 92.963 | 58 | 1.53818 | 88.13354 | 30.6439774 |
| 2 | 1.5 | 0.023449 | 3.6836 | 390.85 | 2.488 | 93.276 | 87 | 1.54413 | 88.47464 | 37.4891545 |
| 3 | 2 | 0.027196 | 4.9072 | 390.51 | 2.164 | 93.616 | 116 | 1.54768 | 88.67826 | 43.2555368 |
| 4 | 2.5 | 0.030498 | 6.1303 | 390.28 | 1.942 | 93.851 | 145 | 1.55011 | 88.81744 | 48.336877 |
| 5 | 3 | 0.033482 | 7.3531 | 390.11 | 1.776 | 94.024 | 174 | 1.55191 | 88.92031 | 52.9319148 |
| 6 | 3.5 | 0.036227 | 8.5756 | 389.97 | 1.647 | 94.162 | 203 | 1.55330 | 89.00032 | 57.157942 |
| 7 | 4 | 0.038782 | 9.798 | 389.86 | 1.543 | 94.268 | 232 | 1.55443 | 89.06480 | 61.0890403 |
| 8 | 4.5 | 0.041182 | 11.02 | 389.76 | 1.457 | 94.366 | 261 | 1.55536 | 89.11832 | 64.7867893 |
| 9 | 5 | 0.043452 | 12.242 | 389.69 | 1.383 | 94.444 | 290 | 1.55615 | 89.16357 | 68.2809525 |
| 10 | 5.5 | 0.04561 | 13.464 | 389.62 | 1.320 | 94.507 | 319 | 1.55683 | 89.20250 | 71.6035594 |
| 11 | 6 | 0.047673 | 14.686 | 389.57 | 1.265 | 94.560 | 348 | 1.55742 | 89.23643 | 74.7746678 |
| 12 | 6.5 | 0.049651 | 15.908 | 389.52 | 1.216 | 94.605 | 377 | 1.55795 | 89.26637 | 77.8156963 |
| 13 | 7 | 0.051555 | 17.13 | 389.49 | 1.172 | 94.644 | 406 | 1.55841 | 89.29303 | 80.7394342 |
| 14 | 7.5 | 0.053392 | 18.351 | 389.43 | 1.133 | 94.698 | 435 | 1.55883 | 89.31713 | 83.5783624 |
| 15 | 8 | 0.055168 | 19.573 | 389.40 | 1.098 | 94.726 | 464 | 1.55921 | 89.33879 | 86.305654 |
| 16 | 8.5 | 0.05689 | 20.794 | 389.36 | 1.065 | 94.769 | 493 | 1.55956 | 89.35863 | 88.9647515 |
| 17 | 9 | 0.058562 | 22.016 | 389.34 | 1.036 | 94.790 | 522 | 1.55987 | 89.37667 | 91.5286211 |
| 18 | 9.5 | 0.060188 | 23.237 | 389.30 | 1.008 | 94.826 | 551 | 1.56016 | 89.39338 | 94.0385709 |
| 19 | 10 | 0.061772 | 24.459 | 389.29 | 0.983 | 94.841 | 580 | 1.56043 | 89.40871 | 98.4858405 |
| 20 | 10.5 | 0.063317 | 25.68 | 389.26 | 0.960 | 94.871 | 609 | 1.56068 | 89.42302 | 98.8483708 |
| 21 | 11 | 0.064825 | 26.901 | 389.23 | 0.938 | 94.898 | 638 | 1.56091 | 89.43635 | 101.175113 |
| 22 | 11.5 | 0.066299 | 28.123 | 389.22 | 0.918 | 94.909 | 667 | 1.56113 | 89.44872 | 103.434005 |
| 23 | 12 | 0.067742 | 29.344 | 389.20 | 0.898 | 94.932 | 696 | 1.56133 | 89.46038 | 105.657723 |
| 24 | 12.5 | 0.069153 | 30.565 | 389.18 | 0.881 | 94.953 | 725 | 1.56152 | 89.47134 | 107.838559 |
| 25 | 13 | 0.07054 | 31.786 | 389.16 | 0.864 | 94.972 | 754 | 1.56170 | 89.48164 | 109.969581 |

Diagrams produced using the values from Table 4 are shown in FIGS. 1 to 5.

FIG. 1 is in this respect a diagram of the relationship $\Delta L$ to R/$\omega$;

FIG. 2 is in this respect a diagram of the relationship $\omega\sigma$ to $\varphi$;

FIG. 3 is a diagram of the relationship $\omega\sigma$ to $\Delta L/(R/\omega)$;

FIG. 4 Is a diagram of the relationship $\omega\sigma$ to $\Delta L$; and

FIG. 5 is a diagram of the relationship $\omega\sigma$ to R/$\omega$.

The invention claimed is:

1. A method for determining the electrical conductivity in samples by means of an eddy current sensor in which an alternating electrical field is excited by an alternating electrical voltage applied to a transmitter coil at a known measurement frequency $\omega$ and an alternating electromagnetic field which is directed against the alternating electrical field is thereby formed which is detected by a receiver coil or by a suitable detector and the complex impedance Z=R+jX is determined wherein this procedure is carried out at different measurement frequencies $\omega$ once in air and once at the same measurement frequencies at a calibration body with a known electrical conductivity $\sigma$, and wherein a determination of the electrical conductivity $\sigma$ of a sample is performed in accordance with one of the following:

1) differences of the real and imaginary portions $\Delta R$ and $\Delta X$ of the measured values in air and over the calibration body are divided by the respective measurement frequency $\omega$; wherein a product $\omega\sigma$ is associated with each value pair $\Delta R/\omega$ and $\Delta X/\omega = \Delta L$ in accordance with the associated measurement frequency $\omega$ and the known conductivity $\sigma$ of the calibration body and a $\omega\sigma$ locus shown in a Nyquist diagram with these value pairs;

wherein
a value pair $\Delta R/\omega$ and $\Delta X/\omega$ of the values in air is formed at the measured values over the sample at a measured impedance Z at a measurement frequency $\omega$ of a sample with an unknown conductivity $\sigma$ and a point from the $\omega\sigma$ locus and thus a $\omega\sigma$ value is associated with this value pair $\Delta R/\omega$ and $\Delta X/\omega = \Delta L$ and the unknown electrical conductivity $\sigma$ of the sample material is determined from this using the known measurement frequency $\omega$; and 2) on the calibration at a calibration body and a measurement at a sample, the phase angle $\varphi = \tan(\Delta X/\Delta R)$ is calculated and the function of the product $\omega\sigma = f(\varphi)$ is determined instead of the $\omega\sigma$ locus, with a product $\omega\sigma$ being associated with the phase angle $\varphi$ on the measurement of an unknown conductivity $\sigma$ of the sample material with this function and thus the electrical conductivity $\sigma$ of the sample being determined at the known measurement frequency $\omega$; and 3) on the calibration at a calibration body and a measurement at a sample, the quotient $q = \Delta X/\Delta R$ or its reciprocal $1/q$ is calculated and, instead of the $\omega\sigma$ locus, the function of the product $\omega\sigma = f(q)$ or $\omega\sigma = f(1/q)$ is determined and a product $\omega\sigma$ is associated with the quotient q or $1/q$ on the measurement of an unknown conductivity $\sigma$ of a sample with this function $f(q)$ or $f(1/q)$ and thus the electrical conductivity $\sigma$ of the sample material is determined.

2. A method in accordance with claim 1, characterized in that the respective measurement frequency $\omega$ is selected in dependence on the respective measurement range of the conductivity $\sigma$ such that the product $\omega\sigma$ lies within the limits of the previously determined $\omega\sigma$ locus.

3. A method in accordance with claim 1, characterized in that only the difference of the real portion $\Delta R/\omega$ is determined in the calibration at a calibration body and on a measurement at a sample and, instead of the $\omega\sigma$ locus, the function of the product $\omega\sigma = f(\Delta R/\omega)$ is determined, with a product $\omega\sigma$ being associated with the difference $\Delta R/\omega$ on the measurement of an unknown conductivity $\sigma$ of a sample with this function and with thus the electrical conductivity $\sigma$ of the sample being determined.

4. A method in accordance with claim 1, characterized in that the difference of the imaginary portion $\Delta X/\omega 32 \Delta L$ is determined on the calibration at a calibration body and on a measurement at a sample and, instead of the $\omega\sigma$ locus, the function of the product $\omega\sigma = f(\Delta L)$ is determined, with a product $\omega\sigma$ being associated with the difference $\Delta L$ on the measurement of an unknown conductivity $\sigma$ of a sample with this function and thus the electrical conductivity $\sigma$ of the sample being determined.

5. A method in accordance with claim 1, characterized in that, instead of the circular frequency $\omega = 2nf$, the frequency f is utilized in the calculation of the values of the locus and of the derived functions, that is, work is carried out with $f\sigma$ instead of $\omega\sigma$.

6. A method in accordance with claim 1, characterized in that a calibration is carried out at a calibration body having a known electrical conductivity $\sigma$ in air for all measurement frequencies f, $\omega$.

* * * * *